US008691770B2

(12) United States Patent
Bertel

(10) Patent No.: US 8,691,770 B2
(45) Date of Patent: Apr. 8, 2014

(54) METHOD FOR PROCESSING MICROBIOLOGICALLY PRODUCED CYCLIC OLIGOPEPTIDES

(75) Inventor: Stephan Bertel, Kundl (AT)

(73) Assignee: Sandoz AG, Basel (CH)

( * ) Notice: Subject to any disclaimer, the term of this patent is extended or adjusted under 35 U.S.C. 154(b) by 283 days.

(21) Appl. No.: 13/055,715

(22) PCT Filed: Jul. 29, 2009

(86) PCT No.: PCT/EP2009/059826
§ 371 (c)(1),
(2), (4) Date: Jan. 25, 2011

(87) PCT Pub. No.: WO2010/012786
PCT Pub. Date: Feb. 4, 2010

(65) Prior Publication Data
US 2011/0124575 A1 May 26, 2011

(30) Foreign Application Priority Data
Jul. 29, 2008 (EP) .................................... 08161348

(51) Int. Cl.
*A61K 38/13* (2006.01)
*A61K 38/12* (2006.01)
*C07K 5/00* (2006.01)
*C07K 7/00* (2006.01)
*C07K 16/00* (2006.01)
*C07K 17/00* (2006.01)
*C07K 1/14* (2006.01)
*C07K 7/64* (2006.01)

(52) U.S. Cl.
CPC ............... *C07K 1/145* (2013.01); *C07K 7/645* (2013.01)
USPC ......................................... 514/20.5; 530/321

(58) Field of Classification Search
CPC .................................. C07K 1/145; C07K 7/645
See application file for complete search history.

(56) References Cited

U.S. PATENT DOCUMENTS

| | | | | |
|---|---|---|---|---|
| 2,503,215 A | * | 4/1950 | Pierotti et al. ................. | 540/324 |
| 4,144,138 A | * | 3/1979 | Rao et al. ........................ | 203/46 |
| 5,156,960 A | | 10/1992 | Jekkel nee Bokany et al. | |
| 6,998,385 B2 | * | 2/2006 | Naicker et al. ................. | 514/6.9 |
| 2002/0162789 A1 | | 11/2002 | Keri | |

FOREIGN PATENT DOCUMENTS

| | | |
|---|---|---|
| DE | 298276 | 3/1919 |
| DE | 2455859 A1 | 6/1975 |
| EP | 507968 | 6/1991 |
| EP | 725076 | 1/1995 |
| EP | 888382 | 9/1997 |
| EP | 888382 A | 9/1997 |
| WO | 9416091 A | 7/1994 |
| WO | 9734918 A1 | 9/1997 |
| WO | 9746575 | 12/1997 |
| WO | 2006063470 A | 6/2006 |

OTHER PUBLICATIONS

Burfield et al. Drying of Grossly Wet Ether Extracts. J. Chem. Ed., Aug. 1982, vol. 59, No. 8, pp. 703-704.*
Husak et al. Crystalline structures of two new cyclosporin clathrate. Collect. Czech. Chem Commun. 2000. vol. 65, pp. 1950-1958.*
International Search Report and Written Opinion (completed Oct. 22, 2009).
Jegorov, Journal of Inclusion Phenomena and Macrocyclic Chemistry, vol. 37, 2000, pp. 137-153.
Kuyukina, "Recovery of *Rhodococcus* biosurfactants using methyl tertiary-butyl ether extraction", Journal of Microbiological Methods, Aug. 2001, vol. 46, No. 2, pp. 149-156.

* cited by examiner

*Primary Examiner* — Marcela M Cordero Garcia
(74) *Attorney, Agent, or Firm* — Jeffrey S. Melcher; Manelli Selter PLLC

(57) ABSTRACT

The present invention relates to a method for processing microbiologically produced, non-polar, cyclic oligopeptides comprising the step of a) extracting the entire fermentation broth incident to the microbiological production process using a liquid extractant that contains ether and is immiscible with water, wherein the amount of extractant is sufficient to form a two-phase system together with the total fermentation broth, and novel solvates of cyclosporin A and methyl-t-butyl ether.

15 Claims, 2 Drawing Sheets

METHOD FOR PROCESSING MICROBIOLOGICALLY PRODUCED CYCLIC OLIGOPEPTIDES

CROSS-REFERENCE TO RELATED APPLICATIONS

This application is a national stage entry under 35 U.S.C. 371 of International Application No. PCT/EP2009/059826, filed 29 Jul. 2009, designating the United States. This application claims foreign priority under 35 U.S.C. 119 and 365 to European Patent Application No. 08161348.1, filed 29 Jul. 2008. The complete contents of these applications are incorporated herein by reference.

The present invention relates to methods of processing microbiologically produced, non-polar, cyclic oligopeptides comprising the step of: a) extracting the entire fermentation broth or mash accumulating in the microbiological production process with a liquid, ether-containing extractant which is immiscible with water, wherein the amount of extractant is sufficient to form a two-phase system together with the total fermentation broth, and to novel solvates of cyclosporin A and methyl-t-butyl ether.

Cyclic oligopeptides, in particular undecapeptides, have long been known inter alia as microbiological metabolites. Of the undecapeptides, in particular cyclosporins have become important.

Cyclosporins, in particular cyclosporin A, are precious, pharmaceutical active substances which can be used as immunosuppressants, in particular in organ transplantations. Cyclosporins are also suitable for the treatment of diseases, such as diabetes and psoriasis, and numerous autoimmune diseases, such as rheumatoid arthritis and chronic inflammations. On account of their inhibitory effect against the human immunodeficiency virus (HIV), cyclosporins, in particular cyclosporin A, are also suited to combat diseases caused by it. Furthermore, cyclosporins, in particular cyclosporin A, have shown to have a pharmacological effect with respect to the sensitization of cancer cells to chemotherapeutic agents, such as vincristine or daunorubicine. The neuroprotective and regenerative properties of cyclosporins, in particular cyclosporin A, can also be used for various neurological indications, such as Alzheimer's disease, amyotrophic lateral sclerosis and Parkinson's disease.

As mentioned above, cyclic undecapeptides, such as cyclosporins, can be produced by microbiological processes.

In particular, cyclosporin A can be produced by means of a strain of the fungal species, i.e. *Cylindrocarpon lucidum Booth*, or a strain of the fungal species, i.e. *Tolypocladium inflatum Gams*. This strain of the *Tolypocladium* fungal species was originally referred to as a strain of the *Trichoderma polysporum* fungal species, which was deposited under number NRRL 8044 with the United States Department of Agriculture (Northern Research and Development Division), Peoria, Ill., U.S.A. The former strain of the fungal species, i.e. *Cylindrocarpon lucium Booth*, was also deposited with the United States Department of Agriculture (Northern Research and Development Division), Peoria, Ill., U.S.A., namely under no. NRRL 5760. Further strains for the microbiological production of cyclosporins, in particular cyclosporin A, are strains of the fungal species *Tolypocladium geodes, Tolypocladium cylindrosporum* and *Tolypocladium* sp. LeA3, the latter strain being deposited under number CBS 630.92 with the depository of the Central Office for Mold Cultures in Holland in accordance with the Budapest Treaty.

The large-scale production of cyclosporins by microbiological processes is a major significance. For this reason, a variety of experiments have been conducted to improve the microbiological production by discovering and cultivating efficient strains of said fungal species or of novel fungal species. The above mentioned strains are examples of these efforts.

However, what is important in connection with a large-scale, microbiological production of cyclosporins is not only an effective fermentation process but also an effective processing of the metabolites thus obtained.

According to the methods known from DOS 2455859 and DD-B-298276, for example, and serving for isolating cyclosporins, in particular cyclosporin A, from the total fermentation broth, i.e. from the culture broth, it is possible to either separate the biomass with the product from the culture broth by filtration or centrifugation or process the entire fermentation broth, i.e. without separating the biomass.

According to the first process variant, the separated biomass including the metabolites is subjected to a preferably repeated extraction with methanol or acetone and the separated extract is preferably concentrated up to an aqueous residue to be extracted, preferably several times, with ethylene chloride or chloroform, for example. It is preferred to correspondingly extract the culture filtrate separated from the biomass as well.

According to the second process variant in which the biomass is not separated, the culture broth, i.e. the total fermentation broth, is extracted inter alia with the above mentioned solvents, i.e. ethylene chloride or chloroform, and the separated, organic phase is chromatographed after the concentration several times on different stationary column packings with different eluents for further processing. What is in consideration here is Sephadex LH-20 as a stationary column material with methanol as the eluent and aluminium oxide as the column material with toluene/ethyl acetate as the eluent.

Corresponding chromatographic processing can also be made with the former processing variant, the residue collected from the ethylene chloride or chloroform extracts being purified by means of the column material, i.e. silica gel, in combination with the chloroform eluent and the Sephadex LH-20 column material in combination with the methanol eluent and being further separated into the desired products, preferably cyclosporin A.

Compared with these previously known processing methods, the object was to provide technologically advantageous, environmentally compatible and efficient processing methods for microbiologically produced, cyclic oligopeptides, in particular undecapeptides, such as cyclosporins, with very good yield and purity of the products. In particular, the object was to reduce the number of organic solvents employed and to achieve the recyclability thereof so as to make the processing method inter alia more efficient in ecological terms.

This object is achieved by providing the method according to the invention for processing microbiologically produced, non-polar, cyclic oligopeptides, comprising the step of a) extracting the entire fermentation broth accumulating in the microbiological production with a liquid, ether-containing extractant which is immiscible with water, wherein the amount of extractant is sufficient to form a two-phase system together with the total fermentation broth.

Microbiologically produced, non-polar, cyclic oligopeptides having preferably 5 to 15 peptide bonds can be processed according to the method of the invention. According to the invention, the term 'oligopeptide' is understood to mean an organic compound comprising a certain number of peptide bonds, with only preferably two successive nitrogen atoms of the ring system being separated by two intermediate carbon atoms. It is preferred to isolate non-polar, cyclic oligopeptides of 8 to 13 amino acids, more preferably undecapeptides, by means of the processing method according to the invention. This method is particularly well suited for processing the microbiologically produced, non-polar undecapeptides, such as cyclosporins, in particular cyclosporin A.

According to the invention, cyclic oligopeptides, in particular undecapeptides, such as cyclosporins, which as lipophilic compounds have a water solubility of <0.1 g/L water at 25° C., have to be understood as non-polar.

The microbiological production of said products by means of the above mentioned strains of certain fungal species are well known to a person skilled in the art. The German laid-open print 2455859 does not only disclose the cultivation of the fungal strains NRRL 5760 and NRRL 8044 at pages 3-4 but also describes the fermentation process for the production of cyclosporins on pages 4-5 and Example 1.

This also applies to the cultivation of the *Tolypocladium* sp.LeA3 strain, which is disclosed on pages 3-5 of WO 94/16091, and the fermentation process using this fungus for the production of cyclosporins, which follows from Examples 1 and 2 of WO 94/16091. Further microbiological methods are disclosed inter alia in DD-B-298276, EP-A-0507968, U.S. Pat. No. 5,156,960.

According to the invention, the desired products can be obtained by extraction from the culture broth, i.e. the entire fermentation broth accumulating in the microbiological production. For this purpose, the total fermentation broth is mixed with a liquid, ether-containing extractant which is immiscible with water, wherein the amount of extractant is sufficient to form a 2-phase system together with the total fermentation broth. The person skilled in the art knows that along with the two coexisting liquid phases solid particles from the fermentation process are also present in the above mentioned system, which are contained in the aqueous phase.

According to the invention, a liquid extractant that is immiscible with water is understood to mean an extractant which has at least a miscibility gap with water at 20° C. At said gap, the liquid extractant is at least incompletely miscible with or incompletely soluble in the water such that phase separation occurs.

It is preferred for these ether-containing extractants which are used according to the invention and are immiscible with water to have a density of at most 0.9 g/cm³, preferably a density of 0.6 to 0.85 g/cm³ more preferably of 0.7 to 0.8 g/cm³, each measured at 20° C.

It is preferred for the ether-containing extractant to consist substantially of one or more ethers, more preferably at least one ether, of the general formula

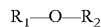

$R_1$—O—$R_2$ wherein $R_1$ and $R_2$ independently represent a linear or branched alkyl residue having $C_1$ to $C_5$ and at least one of the residues $R_1$ and $R_2$ has at least 3 C atoms, preferably at least 4 C atoms.

Particularly preferred ethers which can be used for extraction are represented by at least one ether selected from the group comprising di-isopropyl ether, di-n-propyl ether, di-t-butyl ether, di-iso-butyl ether, methyl-t-butyl ether, ethyl-t-butyl ether, propyl-t-butyl ether and n-butyl-t-butyl ether, the use of methyl-t-butyl ether being particularly preferred.

Thus, a further subject matter of the present invention also relates to the use of liquid, ether-containing extractant which is immiscible with water and preferably has a density of at most 0.9 g/cm³, measured at 20° C., as a means of extracting microbiologically produced, non-polar, cyclic oligopeptides, preferably undecapeptides, more preferably cyclosporins, most preferably cyclosporin A, from the total fermentation broth accumulating in the microbiological production. Preferably the above listed ethers serve for this use according to the invention in the indicated quantities so as to form a 2-phase system with the total fermentation broth.

It is preferred to extract the total fermentation broth at a pH of 7 to 9, preferably 7.5 to 8.5, in particular when cyclosporins, more preferably cyclosporin A, are isolated and processed.

In order to accelerate the phase separation, known, water-soluble wetting agents, e.g. based on polyacrylate, can be added to the total fermentation broth in a sufficient quantity.

The extraction is preferably carried out several times. More preferably, the total extraction broth is preferably extracted twice using the ether-containing extractant.

The total fermentation broth is preferably extracted with the ether-containing extractant that is immiscible with water at room temperature, more preferably at 20 to 30° C.

The extraction of the total fermentation broth can be carried out in conventional apparatuses, the extracts collected during the extraction being combined after the separation of the aqueous phase with the biomass for further processing.

Thus, method step a) is preferably followed by another method step b) according to which the residual water content available in the extract is lowered to less than 1% by weight, preferably to less than 0.3% by weight. Before the residual water content is lowered, the extract is preferably washed with an aqueous solution, preferably with water, to remove optionally present biomass residues. In order to lower the residual water content of an extract optionally purified in this way, it is possible to carry out an azeotropic distillation. In this connection, it is not only the residual water content that is lowered to the desired extent in the extract but the concentration of the microbiologically products product, preferably the cyclosporins, more preferably cyclosporin A, is also increased. A cyclosporin content of preferably 10 to 35% by weight is adjusted with this concentration.

As a result of the azeotropic distillation in step b) it is possible to not only adjust the residual water content in the extract to the desired low water content but also adjust an extract concentration that is advantageous for the subsequent crystallization of the processed product, the product being preferably crystallized as a cyclosporin-ether-solvate. It has been found that the crystallization of cyclosporins as cyclosporin-ether-solvate, and in particular the crystallization of cyclosporin A as cyclosporin A-ether-solvate, is markedly better when the residual water content is less than 1% by weight, in particular less than 0.3% by weight, and provides virtually colorless, white cyclosporin-ether-solvate crystals which can readily be filtrated. The easy filtering capacity of the already very pure cyclosporin-ether-solvate crystals additionally facilitates and shortens the entire processing method.

Correspondingly, the method according to the invention for processing microbiologically produced products, preferably cyclosporins, more preferably cyclosporin A, comprises a further method step c) according to which the extract concentrated in step b) and largely is freed from residual water content is cooled by cooling to temperatures of –10° C. to 15° C., preferably to temperatures of –5° C. to 10° C., for the crystallization as an ether solvate product, preferably cyclosporin-ether-solvate. Preferably, no addition of an organic solvent where the crystals are not soluble to the concentrated extract largely freed from the residual water content is necessary for crystallizing out the cyclosporin-ether-solvate crystals since virtually colorless, white crystals which can be filtrated well are already obtained by cooling the concentrated extract. Where appropriate, the crystals, preferably the cyclosporin-ether-solvate crystals, may be washed for further purification with an organic solvent where the crystals only dissolve slowly.

Where appropriate, the cyclosporin-ether-solvate crystals can be separated into cyclosporins A-Z by known chromatographic purification and crystallization in suitable, known solvents (see in this connection also WO97/46575, EP0725076, EP 0888382).

Correspondingly, a further subject matter of the present invention is the use of crystalline cyclosporin-ether-solvates in the large-scale production of cyclosporins, preferably of cyclosporin A. In particular the crystalline cyclosporin-ether-solvate crystals obtained according to the invention are suitable for this large-scale production.

Surprisingly, the extraction of the total fermentation broth using the ether-containing extractant according to the invention, in particular in connection with the step of lowering the residual water content, enables the crystallization of cyclosporin-ether-solvate crystals which have a good filtering ability and high purity. As a result, the total processing method is markedly facilitated.

A particularly preferred embodiment of the present invention relates to a method of processing microbiologically produced, non-polar cyclosporins, preferably cyclosporin A, comprising the steps of
a) extracting the total fermentation broth accumulating in the microbiological production of cyclosporins with a liquid, ether-containing extractant which is immiscible with water, wherein the amount of extractant is sufficient to form a 2-phase system with the total fermentation broth,
b) lowering the residual water content dissolved in the extract to less than 1% by weight, preferably to less than 0.3% by weight, wherein the extract obtained in step a) can be washed with an aqueous solution, where appropriate, before this residual water content is lowered, and
c) crystallizing the cyclosporins as cyclosporin-ether-solvates, wherein, preferably before the crystallization, the extract obtained in step b) is concentrated to a cyclosporin content of 10 to 25% by weight, based on the total extract, and for the purpose of crystallization the concentrated extract is cooled to temperatures of −10° C. to 15° C., preferably −5° C. to 10° C.

The above mentioned reaction conditions for the individual method steps likewise apply to the processing, preferred according to the invention, of non-polar cyclosporins which have been produced microbiologically, in particular to the processing and isolation of cyclosporin A. This also applies to the employed ether-containing extractants, preferably ethers of the above mentioned general formula.

Correspondingly, virtually colorless, white cyclosporin-ether-solvate crystals which can easily be filtrated can be obtained by means of the preferred processing method according to the invention.

Also, these crystals are in particular suited to be separated into the cyclosporins A-Z by further crystallization in known manner and/or by chromatography processing with known column materials in combination with known, suitable eluents.

It was observed that the isocyclosporin A which can otherwise be separated only with difficulty is markedly depleted in cyclosporin A-ether-solvate crystals.

Correspondingly, a further subject matter of the present invention relates to cyclosporin A containing less than 0.05% by weight of isocyclosporin A, preferably containing 0.04 to 0.05% by weight of isocyclosporin A.

Cyclosporin A which can be obtained according to the processing method of the invention is also distinguished by a relatively small content of cyclosporin H and cyclosporin T.

A further subject matter of the present invention is thus also cyclosporin A, wherein its total content of cyclosporin H and cyclosporin T is less than 0.5% by weight, preferably 0.1 to 0.4% by weight.

Likewise, a further subject matter of the present invention relates to cyclosporin A containing 0.04 to 0.005% by weight isocyclosporin A, wherein the additional total content of cyclosporin H and cyclosporin T is 0.01 to 4% by weight.

This cyclosporin A having the small contents of by-products can preferably be obtained by the processing according to the invention and the further treatment of cyclosporin A-methyl-t-butyl-ether-solvate crystals obtained according to the invention.

By means of the inventive, preferred processing method of non-polar, microbiologically produced cyclosporins, it is thus possible to obtain the cyclosporin-ether-solvate crystals not only with an excellent purity and yields above 90%, preferably ≥95%, but also with a very good manageability of the crystals, since at least 90% of the crystals have a crystal size >10 μm and the median of the grain size distribution is about 60 μm. In order to measure the grain size distribution, 3×1 g of the sample were dispersed in 60 mL of water and measured after the addition of the dispersing unit Hydro 2000S at a stirring speed of 2000 rpm using the "Mastersizer 2000" measurement device of Malvern company. The "Fraunhofer" model of the device manufacturer was used for the purpose of evaluation. The above mentioned values are mean values from 3 such measurements.

A further subject matter of the present invention is thus crystalline cyclosporin A-methyl-t-butyl ether-solvate, at least 90% of the crystals of which have a crystal size >10 μm, wherein preferably the median of the size distribution is between 30 μm and 100 μm, preferably between 40 μm and 80 μm.

As already pointed out, the method according to the invention is in particular suited for processing microbiologically produced cyclosporin A as crystalline cyclosporin A-methyl-t-butyl ether-solvate. It was possible to clearly analyse such crystals by means of X-ray powder diffraction patterns.

X-ray powder diffraction patterns (XRPD) were obtained on an AXS Bruker D-8 X-ray powder diffractometer using the following recording parameters at environmental conditions: tube anode: Cu; generator voltage: 40 kV; generator current: 40 mA, initial angle: 2° 2-theta; end angle: 40° 2-theta; increment: 0.01° 2-theta; time per increment: 2 seconds. The typical accuracy of the 2-theta values is in the range of ±0.1° 2-theta. Therefore, it is possible for a diffraction peak (apex) which is found at 5.0° 2-theta to appear between 4.9 and 5.1° 2-theta on most X-ray diffractometers under standard conditions.

A further subject matter of the present invention is thus crystalline cyclosporin A-methyl-t-butyl ether-solvate which has an X-ray powder diffraction pattern comprising apexes (peaks) at 2 theta angles of 7.0°+/−0.1°, 8.2°+/−0.1°, 11.0°+/−0.1° and 20.5°+/−0.1°, in particular additionally comprising apexes at 2 theta angles of 7.3°+/−0.1°, 11.8°+/−0.1°, 13.3°+/−0.1° and 16.5°+/−0.1°.

The invention also refers to the following subject matters:
1. A method of processing microbiologically produced, non-polar, cyclic oligopeptides comprising the step of
    a) extracting the total fermentation broth accumulating in the microbiological production using a liquid, ether-containing extractant which is immiscible with water at 25° C., wherein the amount of extractant is sufficient to form a two-phase system with the total fermentation broth.
2. A method according to subject matter 1, wherein the non-polar, cyclic oligopeptides are non-polar undecapeptides.
3. A method according to subject matter 2, wherein the non-polar undecapeptides are cyclosporins, preferably cyclosporin A.
4. A method according to any of subject matters 1 to 3, wherein the ether-containing extractant substantially consists of one or more ethers.
5. A method according to subject matter 3 or 4, wherein the ether-containing extractant substantially consists of one or more ethers and the method comprises the further step of:
  b) lowering the residual water content dissolved in the extract to less than 1% by weight, preferably less than 0.3% by weight.
6. A method according to subject matter 5, wherein step b) is made by azeotropic distillation.
7. A method according to subject matter 5 or 6, wherein the extract obtained in step a) is washed with an aqueous solution prior to its further processing in step b).
8. A method according to any of subject matters 5 to 7, wherein the cyclosporin-containing extract is concentrated to a cyclosporin content of 10% by weight-35 by weight, based on the total extract mass.
9. A method according to any of subject matters 1 to 8, wherein the ether used is at least an ether of the general formula $$R_1-O-R_2$$

wherein $R_1$ and $R_2$ independently represent a linear or branched alkyl residue having $C_1$ to $C_5$ and at least one of the residues $R_1$ and $R_2$ includes at least 3 C atoms, preferably at least 4 C atoms.
10. A method according to subject matter 9, wherein the ether used is at least one ether selected from the group comprising diisopropyl ether, di-n-propyl ether, di-t-butyl ether, di-iso-butyl ether, methyl-t-butyl ether, ethyl-t-butyl ether, propyl-t-butyl ether and n-butyl-t-butyl ether.
11. A method according to any of subject matters 5 to 10, wherein the method comprises the further step of:
  c) crystallizing the non-polar, cyclic oligopeptide as ether solvate product.
12. A method according to any of subject matters 5 to 10, wherein the method comprises the further step of:
  c) crystallizing the cyclosporin as cyclosporin-ether-solvate.
13. A method according to subject matter 11 or 12, wherein the concentrated extract is cooled to a temperature of −10° C. to 15° C. for step c).
14. A method according to subject matter 12 or 13, wherein the cyclosporin-ether-solvate crystals obtained according to step c) are washed with organic solvents where the cyclosporin-ether-solvate crystals only dissolve slowly.
15. A method according to any of subject matters 1 to 14, wherein the entire fermentation broth is extracted with the ether-containing extractant several times, preferably two times.
16. A method according to any of subject matters 1 to 15, wherein in the extraction the total fermentation broth has a pH of 7 to 9, preferably 7.5 to 8.5.
17. A method according to any of subject matters 1 to 16, characterized in that the extraction is carried out with an ether-containing extractant at room temperature, preferably at 20 to 30° C.
18. A method according to any of subject matters 12 to 17, characterized in that the cyclosporin-ether-solvate is separated by recrystallization and/or chromatographic processing in cyclosporin A-Z each.
19. Crystalline cyclosporin A-methyl-t-butyl ether-solvate which has an X-ray powder diffraction pattern comprising apexes (peaks) at 2 theta angles of 7.0°+/−0.1°, 8.2°+/−0.1°, 11.0°+/−0.1° and 20.5°+/−0.1°, in particular additionally comprising apexes at 2 theta angles of 7.3°+/−0.1°, 11.8°+/−0.1°, 13.3°+/−0.1° and 16.5°+/−0.1°.
20. Crystalline cyclosporin A-methyl-t-butyl ether-solvate, wherein at least 90% of the crystals have a crystal size of greater than 10 µm (measured by means of laser diffraction, Malvern Mastersizer 2000).
21. Cyclosporin A containing less than 0.05% by weight of isocyclosporin A, preferably containing 0.04-0.005% by weight of isocyclosporin A.
22. Cyclosporin A, wherein its total content of cyclosporin H and cyclosporin T is less than 0.5% by weight, preferably 0.1-0.4% by weight.
23. Cyclosporin A containing 0.04-0.005% by weight of isocyclosporin A, wherein the additional total content of cyclosporin H and cyclosporin T is 0.1-0.4% by weight.
24. Use of crystalline cyclosporin-ether-solvate for the large-scale production of cyclosporins.
25. Use according to subject matter 24 to deplete the by-products, i.e. isocyclosporin A, cyclosporin H and cyclosporin T.
26. Use of a liquid, ether-containing extractant which is immiscible with water at 25° C. for the extraction of non-polar, cyclic oligopeptides accumulating in the microbiological production, preferably cyclosporins, more preferably cyclosporin A, from the entire fermentation broth.

EXAMPLES

The following examples describe special embodiments of the invention in detail; however, they are not intended to limit the invention.

Example 1

Figure 1:
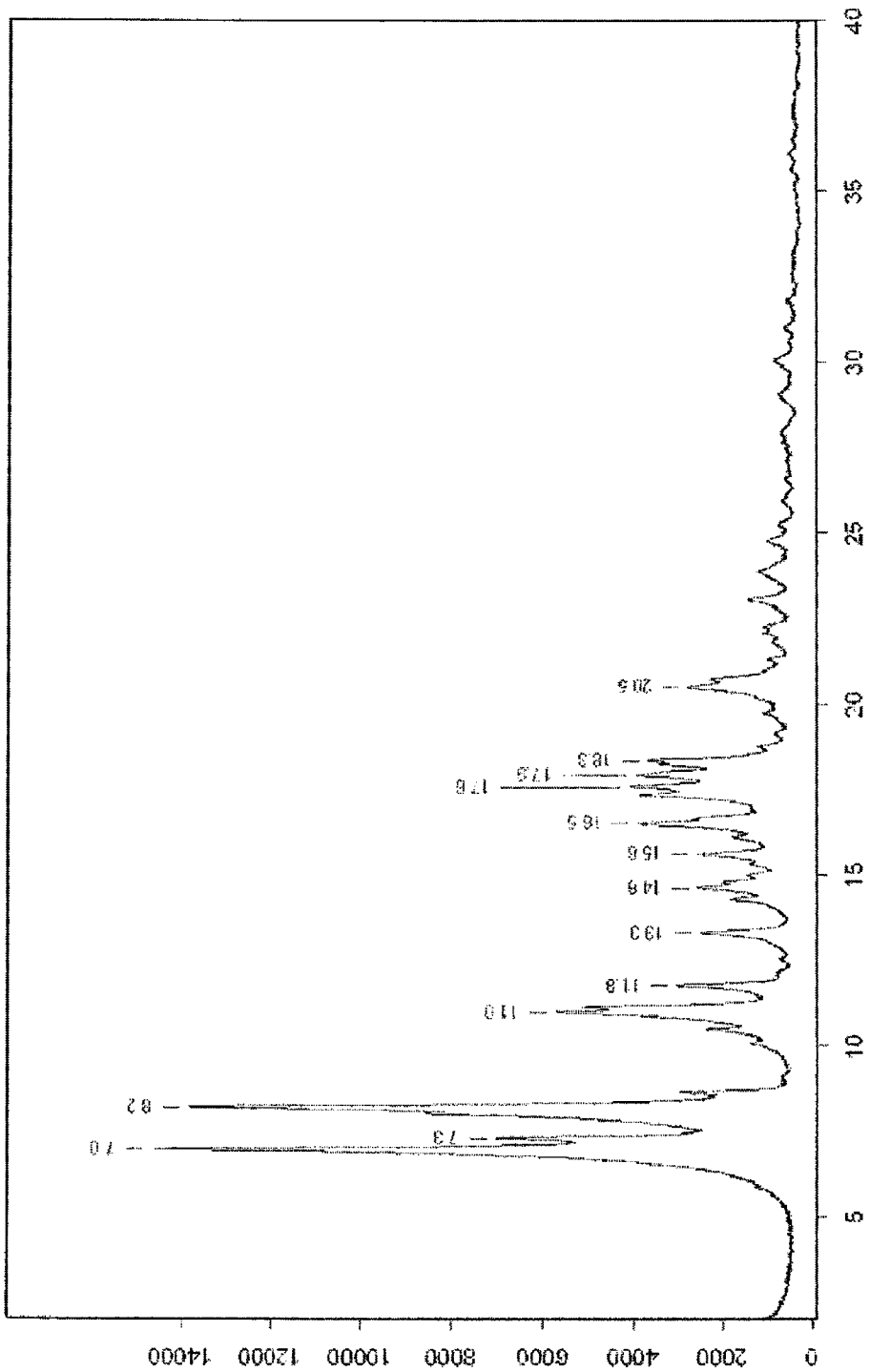
FIG. 1: X-ray powder diffraction pattern of crystalline cyclosporin A-methyl-t-butyl ether-solvate
Figure 2:
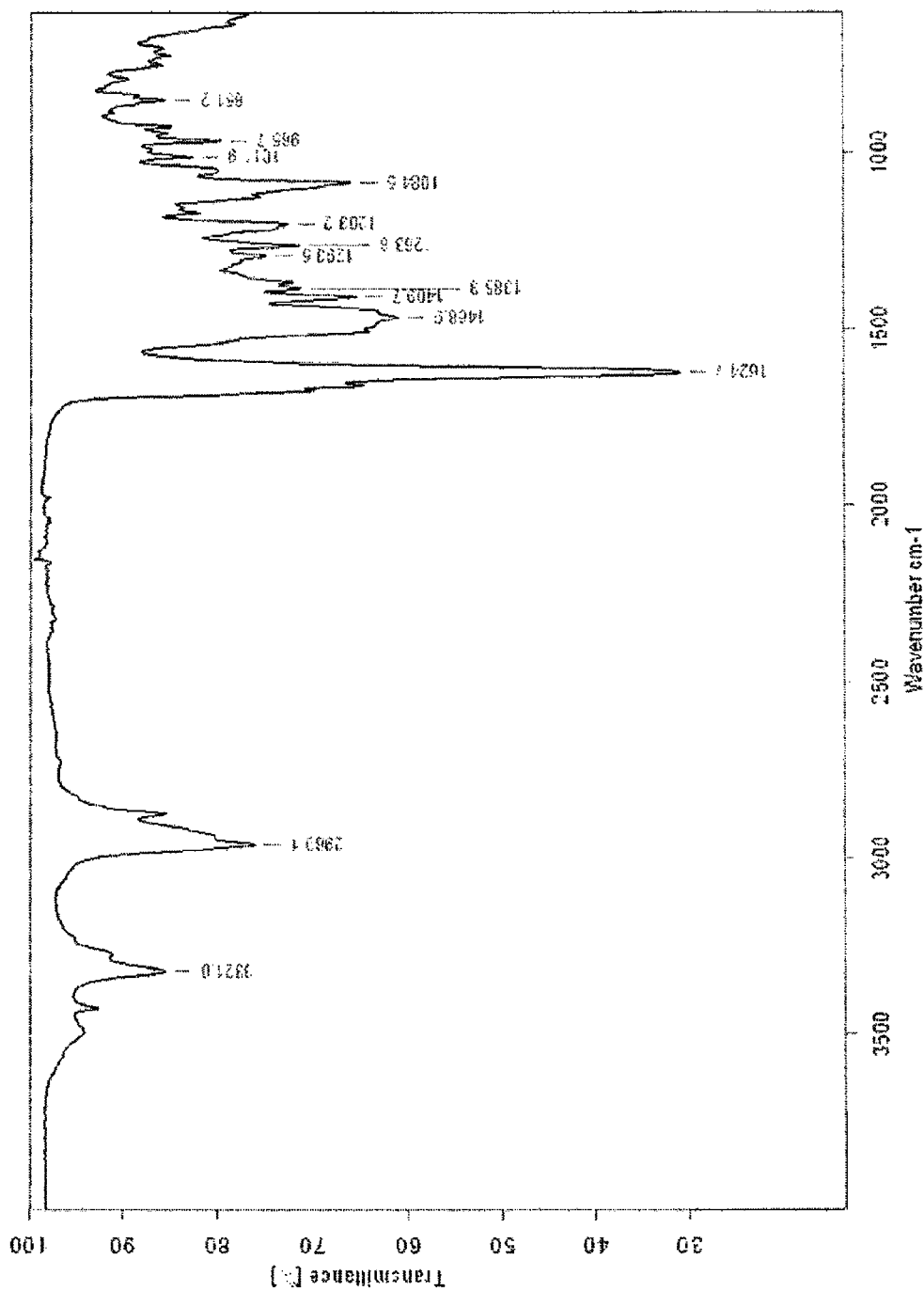
FIG. 2: infrared spectrum of crystalline cyclosporin A-methyl-t-butyl ether-solvate

Extraction of Cyclosporin A from Fermentation Broth 2000 g cyclosporin A-containing fermentation broth as can also be obtained by fermentation of *Tolypocladium inflatum*, for example, were extracted twice with 2000 ml methyl-tert.-butyl ether (MTBE) each in the presence of 4000 ppm of the Clariant MD07/049 polyacrylate. The ether phases were separated in a separating funnel and combined. The cyclosporin A-containing ether phase was washed once with 200 ml water having a pH of about 7, in the separating funnel and the ether phase was concentrated by azeotropic distillation at a temperature of about 53° C. after the filtration so as to achieve a cyclosporin concentration of 150 g/kg. The temperature was then lowered to a value just below the boiling point and kept at this temperature for 2 hours, with MTBE escaping via the distillation head being replaced by fresh one. Thereafter, the solution was concentrated under normal pressure at 53° C. so as to achieve a cyclosporin concentration of 300 g/kg. The residual water content which had been about 1.4% by weight prior to the azeotropic distillation was then below 0.1% by weight. The solution was carefully cooled from 53° C. to 45° C. in 120 minutes, to 40° C. in another 60 minutes, to 30° C. in another 60 minutes and to 0° C. in another 60 minutes. White, crystalline cyclosporin A-MTBE solvate was obtained in a theoretical total yield of about 82%. An infrared spectrum of the resulting crystals is shown in FIG. 2 and a powder X-ray diffraction pattern (XRPD) of the resulting crystals is shown in FIG. 1. The analysis at the interference microscope showed a highly crystalline material having large, birefringent crystals with a mean grain size of about 65 μm.

Example 2

Large-Scale Extraction of Cyclosporin A from Fermentation Broth 510 kg cyclosporin A-containing fermentation broth was extracted twice with 510 L methyl-tert.-butyl ether (MTBE) each, 2.6 kg of the Clariant MD07/049 polyacrylate being added. The ether phases were separated in a 300 L separator in throughfeed and combined. The cyclosporin A-containing ether phase was washed once with 700 L pure water having a pH of about 7, the phases were separated again in a separator and the ether phase was concentrated by azeotropic distillation in a 1000 L thin-layer evaporator at a temperature of about 53° C. so as to achieve a cyclosporin concentration of 100 g/kg. The temperature was then lowered to a value just below the boiling point and this temperature was kept for 2 hours, with MTBE escaping via the distillation head being replaced by fresh one. Thereafter, the solution was concentrated at normal pressure at 53° C. so as to achieve a cyclosporin concentration of 300 g/kg. The residual water content which had been about 1.4% by weight prior to the azeotropic distillation was then 0.1% by weight. Thereafter, the solution was carefully cooled from 53° C. to 45° C. in 120 minutes, to 40° C. in another 60 minutes, to 30° C. in another 60 minutes and to 0° C. in another 60 minutes. 8.55 kg white, crystalline cyclosporin A-MTBE solvate was obtained in a theoretical total yield of about 87%. The isocyclosporin A content was 0.008% by weight, the total content of cyclosporin H and cyclosporin T was 0.28% by weight, which was a highly significant reduction in the content of these contaminations as compared to an extraction method using butyl acetate.

The invention claimed is:

1. A method of processing microbiologically produced cyclosporin A, the method comprising:
   extracting the entire fermentation broth accumulating in the microbiological production with a liquid, ether-containing extractant which is immiscible with water at 25° C., wherein the ether-containing extractant comprises substantially one or more ethers and wherein the amount of extractant is sufficient to form a two-phase system using the total fermentation broth;
   lowering the residual water content dissolved in the extract to less than 1% by weight; and
   crystallizing cyclosporin A-ether-solvate.

2. The method according to claim 1, wherein the ether-containing extractant substantially consists of methyl-tert-butyl ether.

3. The method according to claim 1, wherein the ether-containing extractant substantially consists of methyl-tert-butyl ether and the method comprises the further step of lowering the residual water content dissolved in the extract to less than 0.3% by weight.

4. The method according to claim 1, wherein the ether-containing extractant substantially consists of methyl-tert-butyl ether and the method comprises the further step of lowering the residual water content dissolved in the extract to less than 0.15% by weight.

5. The method according to claim 1, wherein step of lowering the residual water is carried out by azeotropic distillation.

6. The method according to claim 2, wherein the method comprises the further step of crystallizing the cyclosporin as cyclosporin A-methyl-tert-butyl ether-solvate.

7. Cyclosporin A composition obtained according to the method of claim 1 containing crystalline cyclosporin-A-methyl-t-butyl ethersolvate which has an X-ray powder diffraction pattern comprising apexes (peaks) at 2 theta angles of 7.0°+/−0.1 °, 8.2°+/−0.1°, 11.0°+/−0.1 o and 20.5°+/−0.1°, and 0.04 to 0.005% by weight of isocyclosporin A, wherein the additional total content of cyclosporin H and cyclosporin T is 0.1 to 0.4% by weight.

8. A method of producing a cyclosporin A, the method comprising:
   extracting a fermentation broth accumulated in a microbiological production of a cyclosporin with a liquid, ether-containing extractant which is immiscible with water, wherein the ether-containing extractant comprises substantially one or more ethers and wherein the amount of extractant is sufficient to form a two-phase system with the fermentation broth;
   lowering the residual water content dissolved in the extract;
   crystallizing crystalline cyclosporin-ether-solvate from the extractant; and
   separating the cyclosporine from the crystalline cyclosporin-ether-solvate to produce the cyclosporin A.

9. A method of processing microbiologically produced, non-polar, cyclosporin A, the method comprising:
   extracting the entire fermentation broth accumulating in the microbiological production with a liquid, ether-containing extractant which is immiscible with water at 25° C., wherein the ether-containing extractant comprises substantially one or more ethers and wherein the amount of extractant is sufficient to form a two-phase system using the total fermentation broth;
   lowering the residual water content dissolved in the extract to less than 1% by weight; and
   crystallizing the non-polar cyclosporin A as a cyclosporin-ether-solvate.

10. The method according to claim 9, wherein the method comprises lowering the residual water content dissolved in the extract to less than 0.3% by weight.

11. The method according to claim 9, wherein the method comprises lowering the residual water content dissolved in the extract to less than 0.15% by weight.

12. The method according to claim 9, further comprising using azeotropic distillation to lower the residual water content.

13. The method according to claim 8, wherein the cyclosporine is cyclosporin A containing less than 0.05% by weight of isocyclosporin A.

14. The method according to claim 8, wherein the residual water content is reduced by azeotropic distillation.

15. The method according to claim 1, wherein the cyclosporin A-ether-solvate contains less than 0.05% by weight of isocyclosporin A.

* * * * *